(12) United States Patent
Nihei et al.

(10) Patent No.: US 6,520,024 B2
(45) Date of Patent: Feb. 18, 2003

(54) CRACK-TYPE FATIGUE DETECTING SENSOR, METHOD FOR FABRICATING CRACK-TYPE FATIGUE DETECTING SENSOR, AND METHOD FOR ESTIMATING DAMAGE USING CRACK-TYPE FATIGUE DETECTING SENSOR

(75) Inventors: Kanta Nihei, Kobe (JP); Tomohei Kobayashi, Akashi (JP); Hideo Ono, Takasago (JP); Shigeki Koe, Kobe (JP); Akio Murakami, Kobe (JP); Goro Nishiyama, Miki (JP); Yoshinori Dake, Noda (JP)

(73) Assignee: Kawasaki Jukogyo Kabushiki Kaisha, Kobe (JP)

( * ) Notice: Subject to any disclaimer, the term of this patent is extended or adjusted under 35 U.S.C. 154(b) by 0 days.

(21) Appl. No.: 09/822,371

(22) Filed: Mar. 30, 2001

(65) Prior Publication Data

US 2001/0037686 A1 Nov. 8, 2001

(30) Foreign Application Priority Data

Mar. 30, 2000 (JP) ........................................ 2000-094853

(51) Int. Cl.$^7$ .............................................. G01N 19/08
(52) U.S. Cl. ........................................................ 73/799
(58) Field of Search ............................ 73/799, 104, 40, 73/779; 428/76, 209, 156; 324/209

(56) References Cited

U.S. PATENT DOCUMENTS 3,979,949 A  9/1976  Smith ........................ 73/88 R
5,789,680 A * 8/1998 Fujimoto ..................... 73/719
6,289,739 B1 * 9/2001 Fujimoto et al. ............. 73/799

FOREIGN PATENT DOCUMENTS

| JP | 62-265558 | 11/1987 |
| JP | 09-304240 | 11/1997 |
| JP | 10-185854 | 7/1998 |
| JP | 2000-105181 | 4/2000 |

OTHER PUBLICATIONS

Patent Abstracts of Japan vol. 008, No. 257, Nov. 24, 1984 and JP 59 128441 A (Nippon Denshin Denwa Kosha), Jul. 24, 1984.
Patent Abstracts of Japan vol. 010, No. 374, Dec. 12, 1986 and JP 61 167835 A (Mitsubishi Heavy Ind Ltd), Jul. 29, 1986.
European Search Report issued in EP 01 30 2969, Sep. 9, 2002.

* cited by examiner

Primary Examiner—Max Noori
(74) Attorney, Agent, or Firm—Marshall, Gerstein & Borun

(57) ABSTRACT

A crack-type fatigue detecting sensor comprises: a foil substrate having a first surface and a second surface fixed to a member to be tested; and a foil fracture piece having a slit formed in a central portion between opposite end portions in a longitudinal direction thereof such that the slit extends from one side portion toward the other side portion in a width direction thereof perpendicular to the longitudinal direction, wherein the opposite end portions of the fracture piece are respectively fixed to the first surface of the substrate and a portion including the central portion having the slit has a thickness smaller than a thickness of the opposite end portions over a whole width.

13 Claims, 12 Drawing Sheets

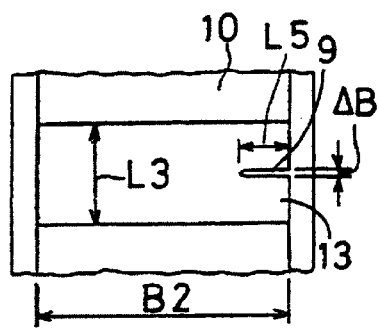
FIG. 10 (1)
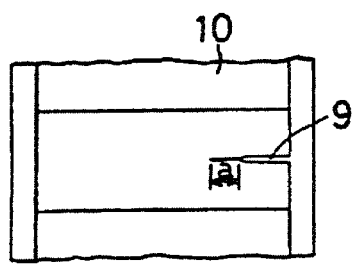
FIG. 10 (2)
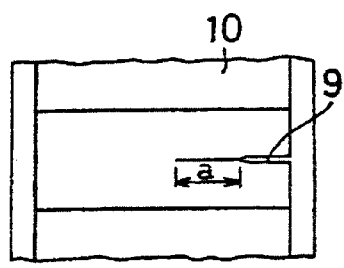
FIG. 10 (3)
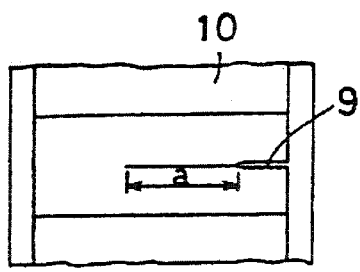
FIG. 10 (4)
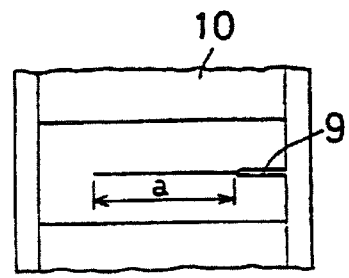
FIG. 10 (5)
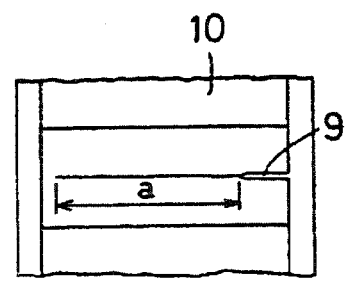
FIG. 10 (6)
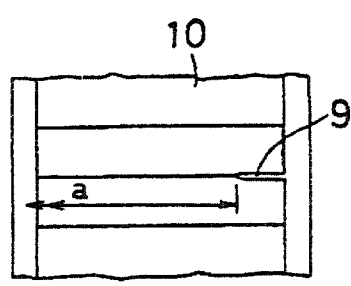
FIG. 10 (7)

FIG. 11 (1) 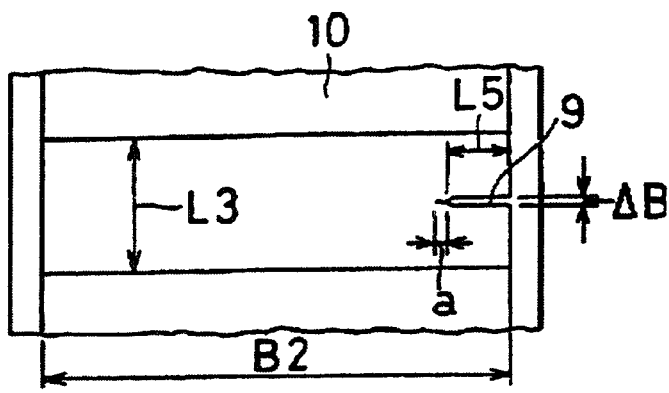
FIG. 11 (2) 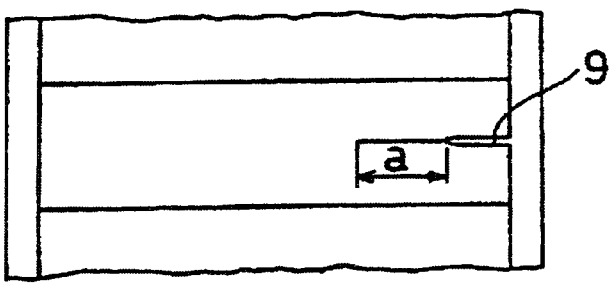
FIG. 11 (3) 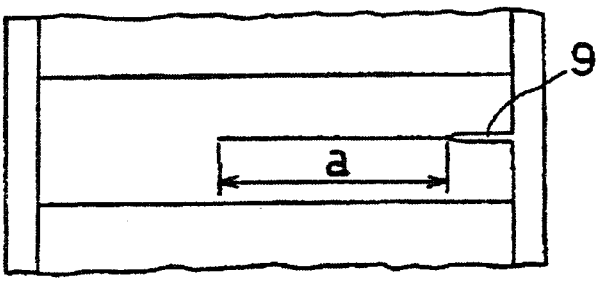
FIG. 11 (4) 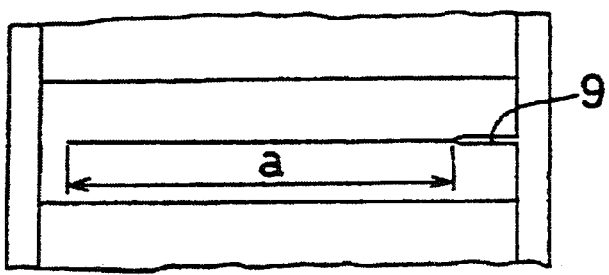
FIG. 11 (5) 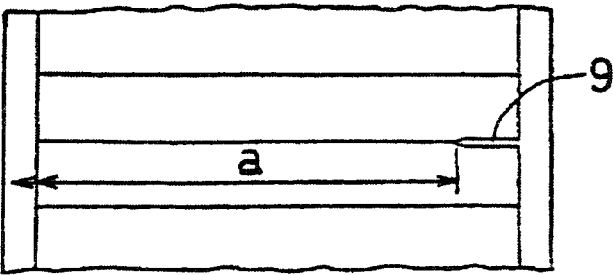

CRACK-TYPE FATIGUE DETECTING SENSOR, METHOD FOR FABRICATING CRACK-TYPE FATIGUE DETECTING SENSOR, AND METHOD FOR ESTIMATING DAMAGE USING CRACK-TYPE FATIGUE DETECTING SENSOR

BACKGROUND OF THE INVENTION

1. Field of the Invention

The present invention relates to a crack-type fatigue detecting sensor, a method for fabricating the crack-type fatigue detecting sensor, and a method for estimating fatigue damage using the crack-type fatigue detecting sensor, which are suitably practiced for measuring damage due to fatigue of various members of a structural component such as a bridge, a machine, a vehicle, an air plane, and the like.

2. Description of the Related Art

A typical prior art is disclosed in Japanese Laid-Open Patent Publication No. Sho. 62-265558. This prior art discloses a crack-type fatigue detecting sensor in which a fracture piece having a slit causing fatigue damage is fixed to a surface of a plate-shaped substrate, a method for fabricating a crack-type fatigue detecting sensor in which opposite end portions (in a longitudinal direction) of a fracture piece having a slit are bonded to a surface of a substrate by bond for fixation, and a method for estimating damage using a crack-type fatigue detecting sensor in which two crack-type fatigue detecting sensors having different crack propagation characteristics are fixed to a member to be tested, lengths of respective cracks propagating during the same period are measured, and damages occurring in the period, due to fatigue of the member to be tested, which are associated with these lengths of crack propagation, are estimated.

Another prior art is disclosed in Japanese laid-Open Patent Publication No. Hei. 9-304240. In this prior art, a thin-plate shaped fracture piece made of a material identical to a material of a structural component for which fatigue damage is predicted and having a slit in a central portion in a longitudinal direction thereof is sandwiched between two synthetic resin thin plates and these are bonded in a region except the central portion of the fracture piece that includes the slit. This test piece is made of the material identical to that of the member to be tested. The crack-type fatigue detecting sensor is fabricated in such a manner that a member having a circular hole in the central portion in the longitudinal direction thereof and the slit extending from the circular hole toward both ends in a width direction thereof is sliced into pieces having a thickness equal to a thickness of the fracture piece, and so formed fracture piece is sandwiched between the two synthetic resin thin plates and the opposite end portions of the fracture piece in the longitudinal direction thereof are bonded to the thin plates. This prior art also discloses a method for estimating damage using the crack-type fatigue detecting sensor, in which the crack-type fatigue detecting sensor is fixed at a position apart from a portion at which stress concentrates, which is so-called a hot spot such as a weld toe, and life of the member to be tested is estimated based on an S–N (=stress–number of repeated load cycles) diagram for the member to be tested created in advance.

Still another prior art is disclosed in Japanese Laid-Open Patent Publication No. Hei. 10-185854. In this prior art, a crack-type fatigue detecting sensor having a plurality of strain gauges spaced apart from one another and placed either in parallel or in series in a direction perpendicular to a direction of a crack of fatigue damage occurring on the member to be tested is attached to the member to be tested, a value of a length of crack propagation occurring on the fracture piece is electrically measured, and damage due to fatigue of the member to be tested is estimated based on this measured value.

A further prior art is disclosed in Japanese Patent No. 2952594. In this prior art, a fracture piece having a slit is provided with strain gauges or crack gauges obtained by placing a plurality of electric resistance wires in parallel with one another in a direction orthogonal to a direction in which a crack initiating from a tip end portion of the slit propagates, for facilitating measurement of a length of crack propagation occurring on the fracture piece, and based on the measured length, damage due to fatigue is estimated.

In the prior art disclosed in the Japanese Laid-Open Patent Publication No. Sho. 62-265558, since the fracture piece, on which no tensile stress remains, is fixed to the substrate, strain occurring on the member to be tested is transmitted to the fracture piece through the substrate, causing the crack to occur at the tip end portion of the slit of the fracture piece, and from the length of the crack, damage due to fatigue of the member to be tested is measured. Therefore, the fracture piece requires tensile stress large enough to cause the crack at the tip end portion of the slit, and strain of the member to be tested that is too small to cause any crack cannot be detected. As a result, sensitivity is low.

In the prior art disclosed in the Japanese laid-Open Paten Publication No. Sho. 9-304240, the fracture piece is sandwiched between two synthetic resin thin plates such that the opposite end portions of the fracture piece in the longitudinal direction are joined to these plates, and one of the thin plates is fixed to the member to be tested. Therefore, the strain occurring on the member to be tested is transmitted to the fracture piece through the thin plate. The strain occurring on the member to be tested is not reliably transmitted to the fracture piece because a part of the strain is absorbed in the thin plate. As a result, sensitivity is low. The crack-type fatigue detecting sensor of this prior art has a large outer shape (70 mm long, 20 mm wide, and 1.5 mm thick). For this reason, this sensor cannot be attached to the member to be tested in proximity to a peripheral end of, for example, a welded bead of this member. Therefore, a position at which damage is measured is limited. Under the circumstance, it is highly probable that the aim cannot be achieved.

In the prior art disclosed in the Japanese laid-Open Patent Publication No. Hei. 10-185854, without an element corresponding to a substrate of the present invention, the fracture piece is directly attached to the member to be tested and the length of crack propagation occurring on the fracture piece is electrically measured by an electric means such as the strain gauge or the electric resistance wire and monitored. The fracture piece has a fixed thickness and a large outer shape (170 mm long, 50 mm wide, and 0.5 mm thick) and the position at which the fatigue damage of the member to be tested is measured is extremely limited.

In the prior art disclosed in the Japanese Patent No. 2952594, although the following two respects are devised to improve the strain sensitivity of the crack initiating from the slit of the sensor attached to the member to be tested, problems associated with its cost and practical use arise. i) Because the crack is difficult to occur in a condition in which only grooves are formed, load is repeatedly subjected to cause the fatigue crack to occur and its tip end portion is made sharp. Still, the crack is difficult to occur under the influence of the compressive stress remaining at the tip end portion of the crack. So, heat treatment (residual stress relief annealing) is carried out to reduce the residual stress. This results in enormous labor and high cost in fabrication. ii) When directly attaching the sensor to the member to be tested, tensile residual stress is given to the sensor. This is sometimes impossible in practice and its management is extremely difficult.

SUMMARY OF THE INVENTION

An object of the present invention is to provide a crack-type fatigue detecting sensor which has a compact configuration and is capable of measurement at a position selected with improved degree of freedom and with high sensitivity, high precision, and high reliability, a method for fabricating the crack-type fatigue detecting sensor, and a method for estimating damage using the crack-type fatigue detecting sensor.

To achieve the above-described problem, there is provided a crack-type fatigue detecting sensor comprising: a foil substrate having a first surface and a second surface fixed to a member to be tested; and a foil fracture piece having a slit formed in a central portion between opposite end portions in a longitudinal direction thereof such that the slit extends from one side portion toward the other side portion in a width direction thereof perpendicular to the longitudinal direction, wherein the opposite end portions of the fracture piece are respectively fixed to the first surface of the substrate and a portion including the central portion having the slit has a thickness smaller than a thickness of the opposite end portions over a whole width.

With such a structure, the opposite end portions of the foil fracture piece having the slit formed in the intermediate portion between the opposite end portions are fixed on the first surface of the foil substrate. The slit extends in the central portion of the fracture piece from one side portion toward the other side portion in the width direction perpendicular to the longitudinal direction. The second surface of the substrate to which the fracture piece is fixed is fixed on the member to be tested. When strain of the member to be tested is transmitted to the fracture piece through the substrate, the crack propagates from the tip end of the slit. Based on the length of the crack, the fatigue damage of the member to be tested can be measured.

The fracture piece is structured such that the intermediate portion including the central portion having the slit has a thickness smaller than a thickness of the opposite end portions over the entire width. Therefore, the strain transmitted from the member to be tested to the opposite end portions through the substrate, causes large stress to be generated in the vicinity of the slit, and this large stress concentrates on the tip end of the slit. Since the large stress concentrating on the tip end of the slit can be thus generated by the strain of the member to be tested, the large stress is generated at the tip end of the slit if the strain occurring on the member to be tested is small. Thereby, fatigue damage caused by small strain of the member to be tested can be measured based on the length of the crack occurring on the fracture piece with high sensitivity, high precision, and high reliability.

It is preferable that in the detecting sensor, the facture piece with tensile stress remaining thereon is fixed to the first surface of the substrate at the opposite end portions.

With such a structure, since the tensile stress remains on the fracture piece, the small strain of the member to be tested can cause the crack to propagate from the tip end of the slit.

Therefore, sensitivity can be further improved. Also, precision can be improved by setting the tensile residual stress of the fracture piece to have a predetermined value or larger.

It is preferable that in the detecting sensor, the fracture piece is directly joined to the first surface of the substrate at the opposite end portions or indirectly joined to the first surface at the opposite end portions via a bonding layer.

With such a structure, since the opposite end portions of the fracture piece is directly joined to the first surface of the substrate or indirectly joined to the first surface via the bonding layer, the strain can be reliably transmitted from the substrate to the opposite end portions of the fracture piece and the tensile stress can be concentratively generated in the central portion of the fracture piece without being dispersed, which facilitates occurrence of the crack.

It is preferable that in the detecting sensor, the fracture piece is provided with a means for electrically measuring a length of crack propagation in a region from a tip end portion of the slit to the other side portion in the width direction, on which the crack develops.

With such a structure, since the measuring means is capable of electrically measuring the length of the crack propagation of the fracture piece, data acquisition and management associated with the crack propagation can be easily carried out. The fatigue detecting sensor is placed on the member to be tested to measure the damage continuously or intermittently on a regular basis over a long time period. Therefore, the measurement operation of the fatigue damage of the member to be tested can be easily performed.

It is preferable that in the detecting sensor, the slit formed in the fracture piece has the tip end portion that is pointed in a direction from the one side portion toward the other side portion in the width direction.

With such a structure, since the tip end of the slit is pointed in the direction from the one side portion to the other side portion in the width direction of the fracture piece, the stress can concentrate on a narrow region at the tip end portion of the slit. Thereby, occurrence of the crack can be facilitated, and sensitivity is further improved.

It is preferable that in the detecting sensor, the fracture piece has one surface and the other surface and a step face is formed between the one surface of the intermediate portion and the one surface of each of the opposite end portions such that step faces are vertically provided with the slit situated between the step faces, and a portion at which each of the step faces and the surface of the intermediate portion intersect continues in a direction toward the other surface of the fracture piece via a convex curved face.

With such a structure, the step face is formed between the surface of the intermediate portion and the surface of the opposite end portions and the convex curved face is formed at the portion at which each of the step faces and the surface of the intermediate portion intersect in the direction toward the other surface of the fracture piece. With the second surface of the substrate fixed to the member to be tested, the strain occurring on the member to be tested is transmitted to the opposite end portions of the fracture piece via the substrate, and then transmitted to the vicinity of the slit in the intermediate portion, causing the crack to occur from the tip end of the slit. Since the intersecting portion has the curved face, the stress transmitted from the opposite end portions to the intermediate portion is relieved on the intersecting portion, i.e., least concentrates thereon. Also, occurrence of the crack on the intersecting portion before occurrence of the crack on the slit is avoided, and reduction of concentration of the stress at the tip end of the slit, caused by dispersion of the stress at the intersecting portion, is minimized to make the stress concentrate on the tip end of the slit, for facilitating occurrence of the crack. As a result, sensitivity can be further improved.

It is preferable that in the detecting sensor, a ratio L3/L4 of a length L3 of the intermediate portion in the longitudinal direction to a length L4 of an unjoined region between the opposite end portions is used to adjust sensitivity in such a manner that the sensitivity is made higher as the ratio L3/L4 is decreased.

With such a structure, by suitably adjusting the length L3 of the intermediate portion with respect to the length L4 of the unjoined region to increase or decrease the ratio L3/L4, the sensitivity can be arbitrarily set. For example, when the ratio L3/L4 is decreased, the sensitivity is made higher. Therefore, the fatigue detecting sensor having high precision and desired sensitivity is realized. The fatigue detecting sensor having the desired sensitivity can be easily fabricated because the length L3 of the intermediate portion can be adjusted without special treatment.

There is also provided a method for fabricating a crack-type fatigue detecting sensor comprising the steps of: forming a foil film having a slit in a central portion between opposite end portions in a longitudinal direction of the foil film, by electroforming plating, the slit extending from one side portion toward the other side portion in a width direction of the foil film; after covering a region of a first surface of the foil film except an intermediate portion including the central portion having the slit and a second surface of the foil film with a resist film, with the intermediate portion exposed, forming a fracture piece including the intermediate portion having a predetermined reduced thickness by etching; and joining the opposite end portions of the fracture piece to the substrate.

With such a procedure, the foil film having the slit in the central portion between the opposite end portions can be formed by electroforming, the metal foil having a uniform thickness can be easily formed. The foil film is etched with the region except the surface of the intermediate portion covered with the resist film, thereby forming the fracture piece including the intermediate portion having the predetermined reduced thickness. Since the etching is employed to reduce the thickness of the intermediate portion, the intermediate portion is isotropically etched to have a uniformly reduced thickness. Thereby, the tensile stress is generated synmetrically with respect to the slit. Consequently, the fatigue detecting sensor with high reliability, on which the crack reliably propagates, is obtained.

There is further provided a method for fabricating a crack-type fatigue detecting sensor comprising the steps of: forming a foil film having a slit in a central portion between opposite end portions in a longitudinal direction of the foil film, the slit extending from one side portion toward the other side portion in a width direction of foil film; after covering a region of a first surface of the foil film except an intermediate portion including the central portion having the slit and a second surface of the foil film with a resist film, with the intermediate portion exposed, forming a fracture piece including the intermediate portion having a predetermined reduced thickness by etching; and joining the opposite end portions of the fracture piece to the substrate made of a material having a linear expansion coefficient lower than a linear expansion coefficient of a material of the fracture piece at a predetermined elevated temperature higher than a normal temperature.

With such a procedure, the fracture piece having the slit in the central portion and including the intermediate portion having the reduced thickness is joined to the substrate made of the metal material having the linear expansion coefficient lower than that of the material of the fracture piece at the opposite end portions in the longitudinal direction, at the predetermined elevated temperature higher than the normal temperature. When the fracture piece and the substrate are cooled to the normal temperature, the tensile stress can remain on the fracture piece. Because the tensile stress remains on the fracture piece, the crack can occur from the tip end of the slit and the fatigue damage can be measured with high sensitivity, if the strain occurring on the member to be tested is small. In addition, since the metal foil is formed by electroforming and the fracture piece is etched to obtain the intermediate portion having the reduced thickness, the sensor can be easily fabricated, at a low cost and in large quantities. Consequently, the sensor of the present invention has superior industrial applicability.

In this method, it is preferable that the fracture piece is directly joined to the substrate at the opposite end portions or indirectly joined to the substrate at the opposite end portions via a bonding layer by electric resistance welding.

With such a procedure, since the fracture piece is directly joined to the first surface of the substrate at the opposite end portions or indirectly joined to the first surface at the opposite end portions via the bonding layer, the strain can be reliably transmitted from the substrate to the opposite end portions of the fracture piece and the tensile stress can be concentratively generated in the central portion of the fracture piece without being dispersed, which facilitates occurrence of the crack.

Also, in this method, it is preferable that a ratio L3/L4 of a length L3 of the intermediate portion of the fracture piece in the longitudinal direction to a length L4 of an unjoined region between the opposite end portions in the longitudinal direction is used to adjust sensitivity in such a manner that the sensitivity is made higher as the ratio L3/L4 is decreased.

With such a procedure, by suitably adjusting the length L3 of the intermediate portion with respect to the length L4 of the unjoined region to increase or decrease the ratio L3/L4, the sensitivity can be arbitrarily set. For example, when the ratio L3/L4 is decreased, the sensitivity is made higher. Therefore, the fatigue detecting sensor having high precision and desired sensitivity is realized. The fatigue detecting sensor having the desired sensitivity can be easily fabricated because the length L of the intermediate portion can be adjusted without special treatment.

There is further provided a method for estimating damage using a crack-type fatigue detecting sensor comprising the steps of: fixing the above-described crack-type fatigue detecting sensor to a member to be tested; measuring a length of crack propagation during a predetermined period; and estimating damage of the member to be tested based on the length of crack propagation.

With such a procedure, the length of the crack propagation can be measured by using the crack-type fatigue detecting sensor with high sensitivity and high precision, and based on the measured length, fatigue damage of the member to be tested is estimated. Therefore, even fatigue caused by the small strain in an initial stage can be detected, and based on the length of the crack with high sensitivity, high precision, and high reliability, the fatigue damage of the member can be estimated.

These objects as well as other objects, features and advantages of the invention will become apparent to those skilled in the art from the following description with reference to the accompanying drawings.

BRIEF DESCRIPTION OF THE DRAWINGS

FIG. 10 is a plan view showing crack propagation states of sample 14 of FIG. 9 at measurement points P1–P7;

FIG. 11 is a plan showing crack propagation states of sample 15 of FIG. 9 at measurement points Q1–Q5;

DETAILED DESCRIPTION OF THE PREFERRED EMBODIMENTS

Figure 1:
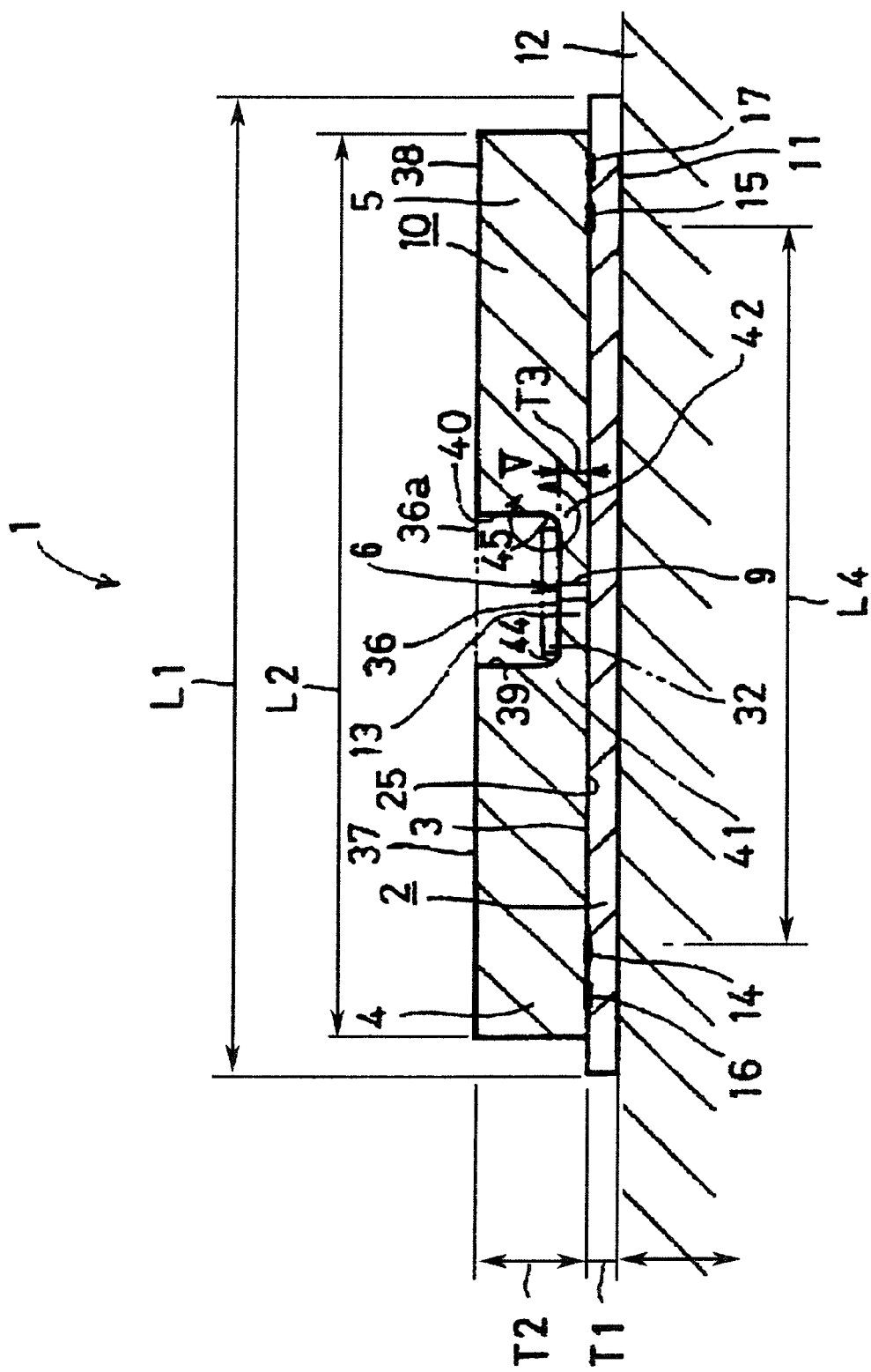
FIG. 1 is a cross-sectional view showing a crack-type fatigue detecting sensor according to an embodiment of the present invention.
Figure 2:
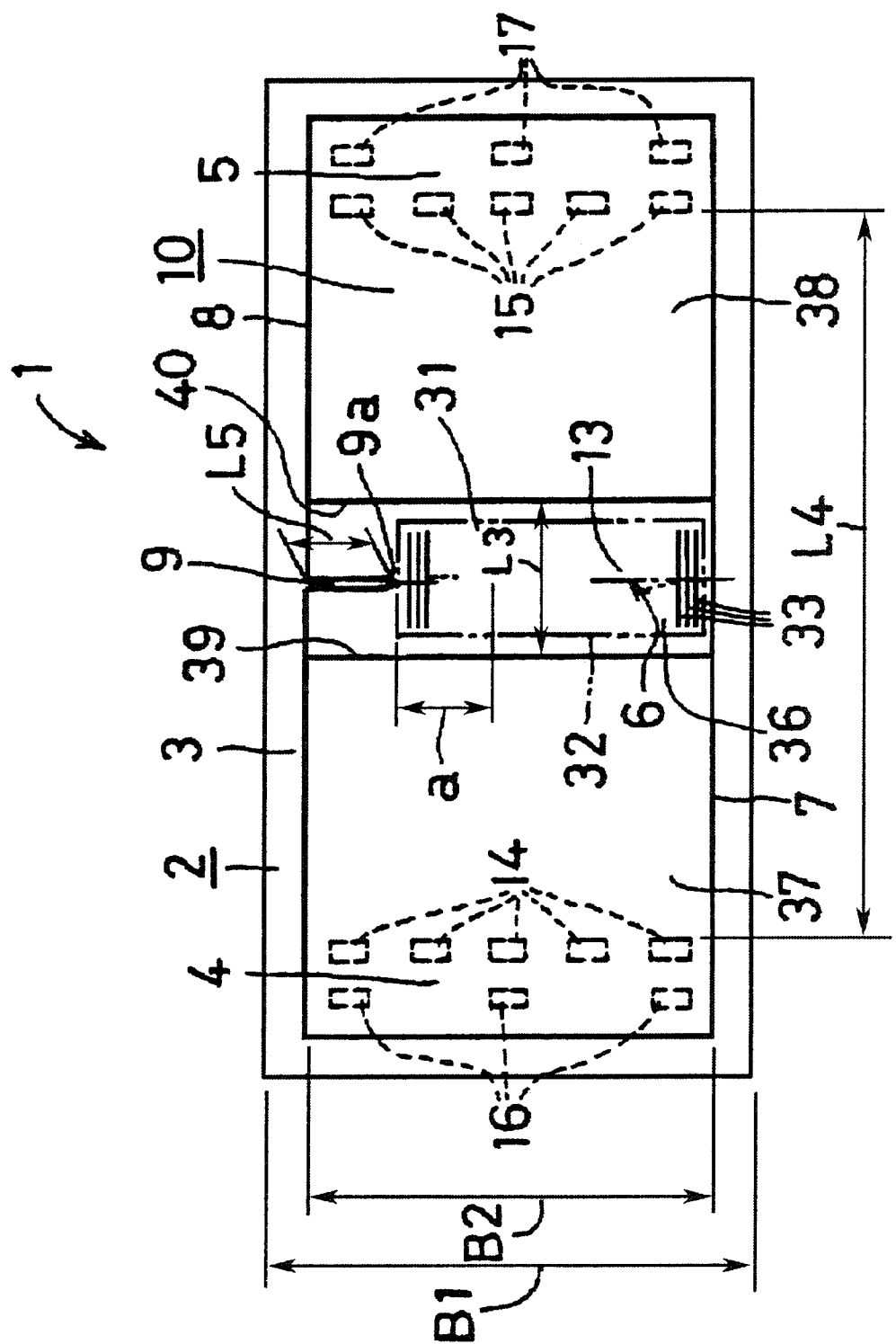
FIG. 2 is a plan view showing the crack-type fatigue detecting sensor of FIG. 1.

FIG. 1 is a cross-sectional view showing a crack-type fatigue detecting sensor 1 according to an embodiment of the present invention and FIG. 2 is a plan view showing the crack-type fatigue detecting sensor 1 of FIG. 1. Hereinafter, a method for fabricating the crack-type fatigue detecting sensor 1 and a method for estimating fatigue damage using the crack-type fatigue detecting sensor 1 will be also described. In order to reduce an endurance test period and cost as well as predict a life of a machine in service, a structural component, or the like and extend its life, it is important to accurately predict the life by non-destructive detection of fatigue damage of the member to be tested. For measurement of the life, i.e., the fatigue damage, the crack-type fatigue detecting sensor (hereinafter referred to as fatigue detecting sensor) of this embodiment is employed.

Referring now to FIGS. 1, 2, the fatigue detecting sensor 1 is shown. In the fatigue detecting sensor 1, a foil fracture piece 10 including a slit 9 formed in a central portion 6 between opposite end portions 4, 5 in a longitudinal direction thereof (right and left direction in FIGS. 1, 2) such that it extends from one side portion 8 toward the other side portion 7 in a width direction thereof perpendicular to the longitudinal direction is fixed on a surface (one surface) 3 of a foil substrate 2 at the opposite end portions 4, 5, and a surface (the other surface) 11 of the substrate 2 is fixed to a member 12 to be tested (member 12). The detecting sensor 1 is capable of measuring fatigue damage of the member 12 based on length a of a crack propagating from the slit 9.

In the fatigue detecting sensor 1, an intermediate portion 13 including the central portion 6 in which the slit 9 of the fracture piece 10 is formed is made thinner than the opposite end portions 4, 5 over the entire width. Thereby, strain transmitted from the member 12 to the opposite end portions 4, 5 causes large stress in the intermediate portion 13, and strain sensitivity and stress sensitivity are improved as mentioned later.

The substrate 2 has a length L1, a width B1, and a thickness T1. In this embodiment, the length L1 is 13.0 mm, the width B1 is 6.0 mm, and the thickness T1 is 0.05 mm. The fracture piece 10 has a length L2, a width B2, and a thickness T2. In this embodiment, the length L2 is 12.0 mm, the width B2 is 5.0 mm, and the thickness T2 is 0.1 mm. The intermediate portion 13 of the fracture piece 10 has a length 3 of 2.0 mm and a thickness T3 of 0.02 mm. The substrate 2 is made of invar or Ni—Fe based alloy and is preferably made of invar. The fracture piece 10 is made of plating metal and is preferably made of pure nickel (Ni).

The opposite end portions 4, 5 of the fracture piece 10 are directly joined on the surface 3 of the substrate 2 by the resistance welding at a plurality of (5 in this embodiment) joint portions 14 and a plurality of (5 in this embodiment) joint portions 15 and at a plurality of (3 in this embodiment) joint portions 16 and a plurality of (3 in this embodiment) joint portions 17 which are respectively situated outwardly of the joint portions 14, 15 in the longitudinal direction. The length L3 of the intermediate portion 13 in the longitudinal direction is determined according to desired sensitivity with respect to the length L4 of an unjoined region between the end portions 4, 5. For example, if the length L3 of the intermediate portion 13 is increased with respect to the length L4 of the unjoined region, then L3/L4 is made larger. The tensile stress generated on the tip end portion 9a of the slit 9 is decreased with an increase in the L3/L4 and sensitivity is correspondingly lowered. Based on this fact, the L3/L4 is determined experimentally or theoretically according to a rate at which the crack propagates from the tip end portion 9a, for facilitating adjustment to obtain desired sensitivity according to the length L3 of the intermediate portion 13.

Figure 3:
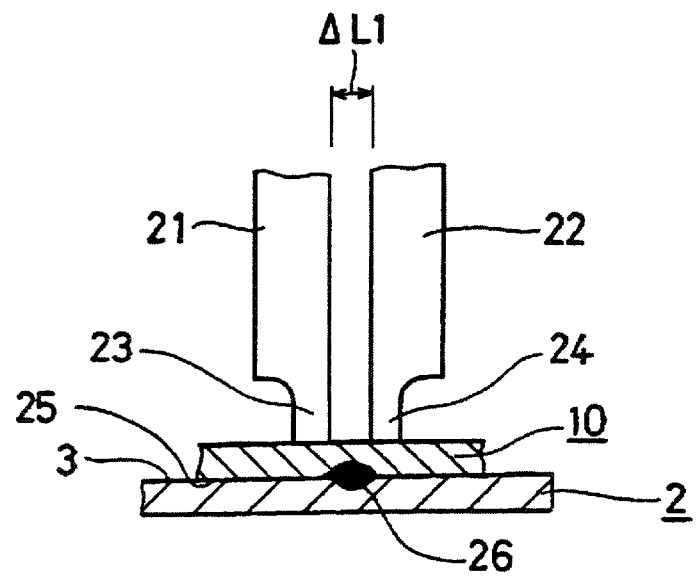
FIG. 3 is a view schematically showing a state in which a substrate and a fracture piece are connected by means of electric wires.

The resistance welding is performed as follows. As shown in simplified FIG. 3, a resistance welder including a pair of electrodes 21, 22 placed in parallel and spaced ΔL1 apart from each other and a power supply (not shown) for applying high voltage across the electrodes 21, 22 is used. Tip end portions 23, 24 of the electrodes 21, 22 are placed on the opposite end portions 4, 5 of the fracture piece 10 placed on the substrate 2 such that the tip end portions 23,24 sandwiches each of the joint portions 14–17 and voltage is applied across the electrodes 21, 22 by the power supply.

Thereby, current conducts through an intermediate portion between the electrodes 21, 22 that is situated between the surface 3 of the substrate 2 and a lower surface 25 of the fracture piece 10 that is opposite to the surface 3 to generate heat and a melted and bonded portion 26 is formed by mechanical joint. The melted and bonded portion 26 forms the joint portions 14–17 at which the substrate 2 and the fracture piece 10 are connected to each other.

The voltage applied across the electrodes 21, 22 by the power supply is, for example, a pulse voltage of 0.62 V. The application time period, which is optimal according to the thicknesses and materials of the substrate 2 and the fracture piece 10, is selected in the range of 8 to 40 msec. Such resistance welding is also called Parallel Gap Resistance Microjoining (PGRM) and is capable of welding a portion between stacked thin-plate shaped members.

In this embodiment, like the inward joint portions 14, 15, joint portions are provided intermittently for prevention of loose of the facture piece 10 caused by local thermal deformation.

In another embodiment of the present invention, the fracture piece 10 having the opposite end portions 4, 5 fixed on the surface of the substrate 2 is provided with a crack propagation length measuring means 32 for electrically measuring the length a of crack propagation in a region 31 in which the crack develops, from the tip end portion 9a of the slit 9 to the other side portion 8 in the width direction.

The measuring means 32 includes a plurality of electric resistance wires 33 extending in the longitudinal direction orthogonal to a direction in which the crack propagates, i.e., a lateral direction. The electric resistance wires 33 are equally spaced apart in the width direction and placed in parallel with one another. The wires 33 have opposite end portions electrically connected in parallel. The wires 33 are covered in sheets with electric insulating synthetic resin, for example, epoxy resin, and bonded to the region 31 by means of bond.

When the crack propagates from the tip end portion 9a of the slit 9, the electric resistance wires 33 are sequentially broken. A variation of a resistance value due to such break, which occurs with an elapse of time, is measured by a measuring instrument (not shown). Thereby, the state of crack propagation can be quantitatively detected.

In still another embodiment of the present invention, the electric resistance wires 33 as the measuring means 32 may be replaced by strain gauges.

Figure 4:
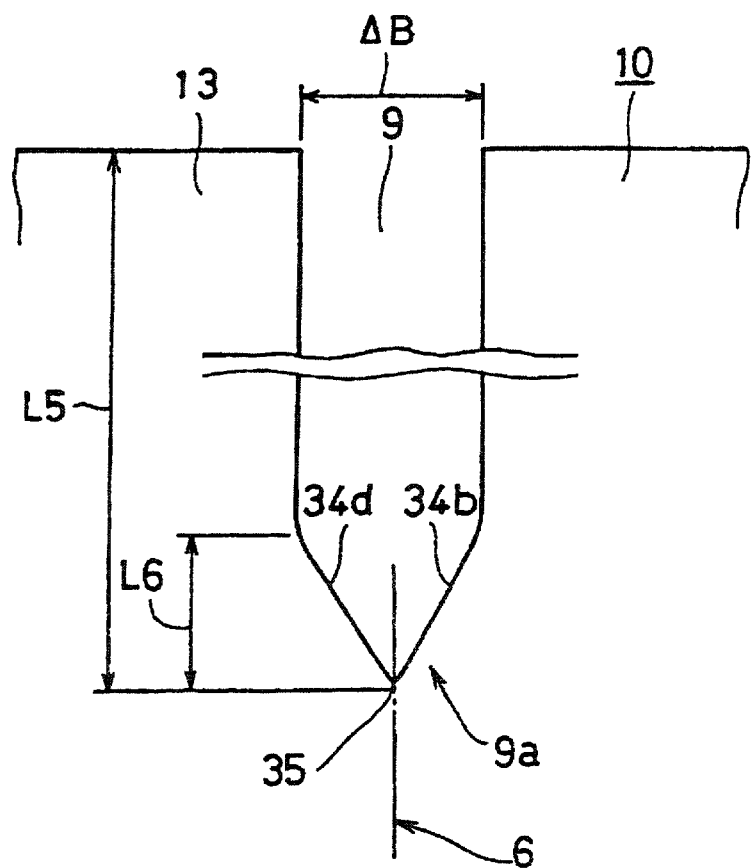
FIG. 4 is an enlarged plan view showing a slit of FIG. 2 and its vicinity.

FIG. 4 is an enlarged plan view showing the slit 9 of FIG. 2 and its vicinity. The slit 9 provided in the fracture piece 10 is formed such that the tip end portion 9a is pointed in a direction from the one side portion 8 toward the other side portion 7 in the width direction. A length L5 of the slit 9 in the width direction is 1.0 mm and the width ΔB parallel with the longitudinal direction is 0.125 mm. The tip end portion 9a has a length L6 of 0.125 mm in the width direction. The tip end portion 9a is substantially equilateral triangle seen in a plan view. At the tip end portion 9a of he slit 9, a pair of opposite faces 34a, 34b which are closer to each other in the direction from the one side portion 8 toward the other side portion 7 in the width direction, intersect at an intersection 35 and forms an acute angle between them. From the intersection 35, the crack occurs.

Since the tip end portion 9a of the slit 9 is thus pointed, stress concentrates on the intersection 35, which facilitates propagation of the crack. Therefore. if the strain transmitted to the fracture piece 10 is small, the crack can easily occur from the intersection 35. Consequently, the sensitivity of the fatigue detecting sensor 1 is improved.

Figure 5:
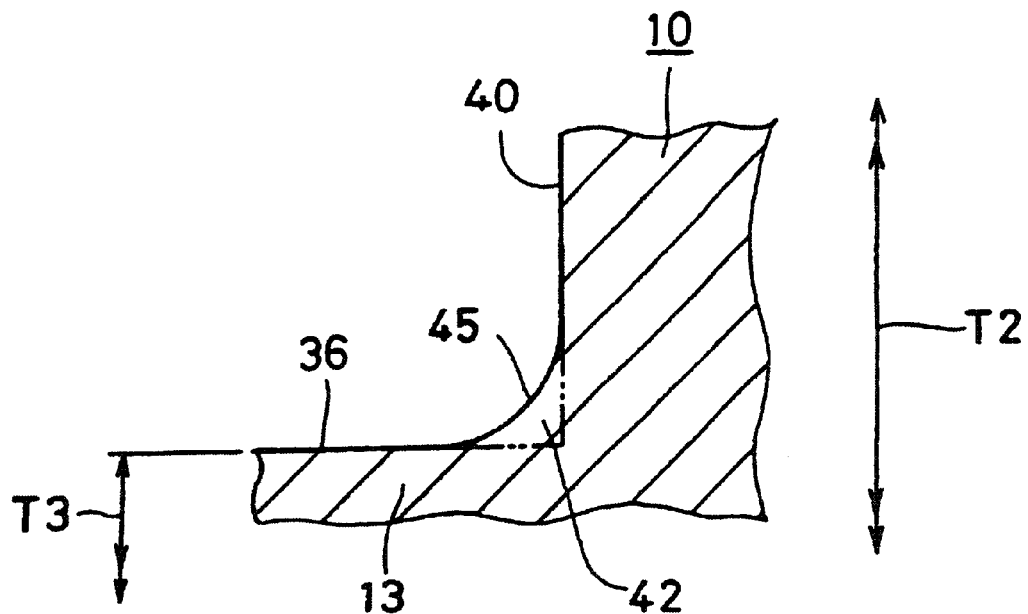
FIG. 5 is an enlarged cross-sectional view showing a section V of FIG. 1.

FIG. 5 is an enlarged cross-sectional view showing a section V of FIG. 1. Referring to FIGS. 1, 2, 5 a step face 39 is formed between a surface 36 of the intermediate portion 13 and a surface 37 of the end portion 4 and a step face 40 is formed between the surface 36 and a surface 38 of the end portion 5 such that the step faces 39, 40 extend in parallel with each other with the slit 9 situated between them. A portion 41 at which the step face 39 and the surface 36 intersect and a portion 42 at which the step face 40 and the surface 36 intersect, respectively continue in a direction toward the lower surface 25 of the fracture piece 10 via convex curved faces 44, 45. The intermediate portion 13 has a thickness T3 of 0.02 mm.

Thus, since the opposite end portions 4, 5 of the fracture piece 10 respectively continue with the surface 36 of the intermediate portion 13 via the step faces 39, 40 and the curved faces 44, 45, and the thickness T3 of the intermediate portion 13 is made smaller than the thickness T2 of the end portions 4, 5 (T2>T3), stress does not concentrate on the portions 41, 42 or is relieved on them, and large stress is generated on the intermediate portion 13.

In fabrication of the fatigue detecting sensor 1, the metal foil made of pure Ni and including the slit 9 formed in the central portion 6 between the end portions 4, 5 such that it extends from the one side portion 8 toward the other side portion 7 is formed by electroforming plating, and then the region (corresponding to the surfaces 37, 38 of the end portions 4, 5) and the surface 25 are covered by a resist film such that a surface (indicated by an imaginary line 36a in FIG. 1) of a portion corresponding to the intermediate portion 13 including the central portion 6 is exposed, and then wet etching is performed to obtain the intermediate portion 13 having a reduced predetermined thickness T3, thereby forming the fracture piece 10.

The end portions 4, 5 of so formed fracture piece 10 are joined to the surface 3 of the substrate 2 made of Invar as a metal material having a linear expansion coefficient lower than that of the fracture piece 10 at a predetermined elevated temperature higher than a normal temperature , for example, 70° C., thereby completing the fatigue detecting sensor 1. The linear expansion coefficient αNi of pure Ni is 13.3× $10^{-6}$/° C. and the linear expansion coefficient αIn of Invar is 1.5×$10^{-6}$/° C.

The substrate 2 and the fracture piece 10 are joined by the electric resistance welding at the joint portions 14–17 as described above. Then, heat is gradually dissipated to lower the temperature to cause the tensile stress to remain on the fracture piece 10. Thereby, loose and bucking of the fracture piece 10 can be prevented. In addition, small strain can cause crack and sensitivity is therefore improved in measurement of the fatigue damage.

Further, since the intermediate portion 13 having the reduced width is formed in the fracture piece 10 by etching, the curved faces 44, 45 are naturally formed at the portions 41, 42, which are consequently R-shaped. The etching is wet etching and the metal foil covered by the resist film is immersed in an etchant. The intermediate portion 13 contact with the etchant is isotropically etched and etching amount is substantially proportional to etching time. This etching proceeds in a direction parallel with the upper surface of the fracture piece 10 as well as in the thickness direction. As a result, the steps faces 39, 40, the curved faces 44, 45, and the surface 36 are formed such that they are smooth and continuous.

Subsequently, relationship between temperature at which the substrate 2 made of Invar and the fracture piece 10 made of pure Ni are joined and tensile residual stress on the intermediate portion 13 will be described below.

Difference $\Delta\delta$ in contraction amount between the substrate 2 and the fracture piece 10 when an elevated temperature during joint is reduced to the normal temperature (room temperature) by $\Delta t$, is represented by:

$$\Delta\delta = (\alpha Ni - \alpha In) \times \Delta t \times L4 = \delta Ni + \delta In \quad (1)$$

Meanwhile, force balance of the substrate 2 and the fracture piece 10 is expressed as:

$$(\delta_{In}/L4) \times E_{In} \times T2 \times B1 = (\delta Ni/L') \times E_{Ni} \times T3 \times B2 \quad (2)$$

$$L' = L3 + (T3/T1) \times L7$$

where, $\Delta t$: difference between temperature at which the substrate 2 and the fracture piece 10 are joined and used temperature (room temperature), $\Delta\delta$: difference in contraction amount associated with joint span S of the substrate 2 and the fracture piece 10 when temperature is reduced by $\Delta t$ $\alpha In$: linear expansion coefficient of the substrate 2 (=1.50×10$^{-6}$[° C.$^{-1}$])

$\alpha Ni$: linear expansion coefficient of the fracture piece 10 (=1.33×10$^{-5}$[° C.$^{-1}$])

L3: length of the intermediate portion 13 of the fracture piece 10

L7: length of (span L4 minus length L3) in the fracture piece 10

L4: joint span of the fracture piece 10 and the substrate 2 (L3+L7)

$\delta_{In}$: amount of span change of the substrate 2 when temperature is reduced by $\Delta t$ after joint $\delta Ni$: amount of span change of the fracture piece 10 when temperature is reduced by $\Delta t$ after joint $E_{In}$: Young's modulus of the substrate 2 (=14,490 [kgf/mm$^2$])

$E_{Ni}$: Young's modulus of the fracture piece 10 (=19,600 [kgf/mm$^2$])

T1: thickness of the opposite end portions 4, 5

T2: thickness of the substrate 2 (fixed)

T3: thickness of the intermediate portion 13

B1: width of the substrate 2 (fixed)

B2: width of the fracture piece 10 (fixed)

Derived from the expressions (1),(2) are:

$$\delta Ni = \{(\alpha Ni - \alpha In) \times \Delta t \times L4\}/[1 + L4/L') \times \{(E_{Ni} \times T3 \times B2)/(E_{In} \times T2 \times B1)\}] \quad (3)$$

$$\delta_{In} = (\alpha Ni - \alpha In) \times \Delta t \times L4 - \delta Ni \quad (4)$$

The tensile residual stress $\sigma Ni,1$ of the intermediate portion 13 of he fracture piece 10 is calculated according to the following expression:

$$\sigma Ni,1 = \epsilon Ni,1 \times E_{Ni} = (\delta Ni/L') \times E_{Ni} \quad (5)$$

The tensile residual stress $\sigma Ni,2$ of the opposite end portions 4, 5 of the fracture piece 10 and compressive residual stress $\sigma_{In}$ is calculated according o the following expressions:

$$\sigma Ni,2 = \epsilon Ni,2 \times E_{Ni} = (T3/T1) \times \epsilon Ni,1 \times E_{Ni} \quad (6)$$

$$\sigma In = \epsilon In \times EIn = (\delta_{In}/L4) \times EIn \quad (7)$$

The tensile residual stress given to the fracture piece 10 of the fatigue detecting sensor 1 is calculated according to the expressions (5), (6). The tensile residual stress is approximately 14–15 kgf/mm$^2$ in the intermediate portion 13 and approximately 3 kgf/mm$^2$ in the opposite end portions 4, 5.

Figure 6:
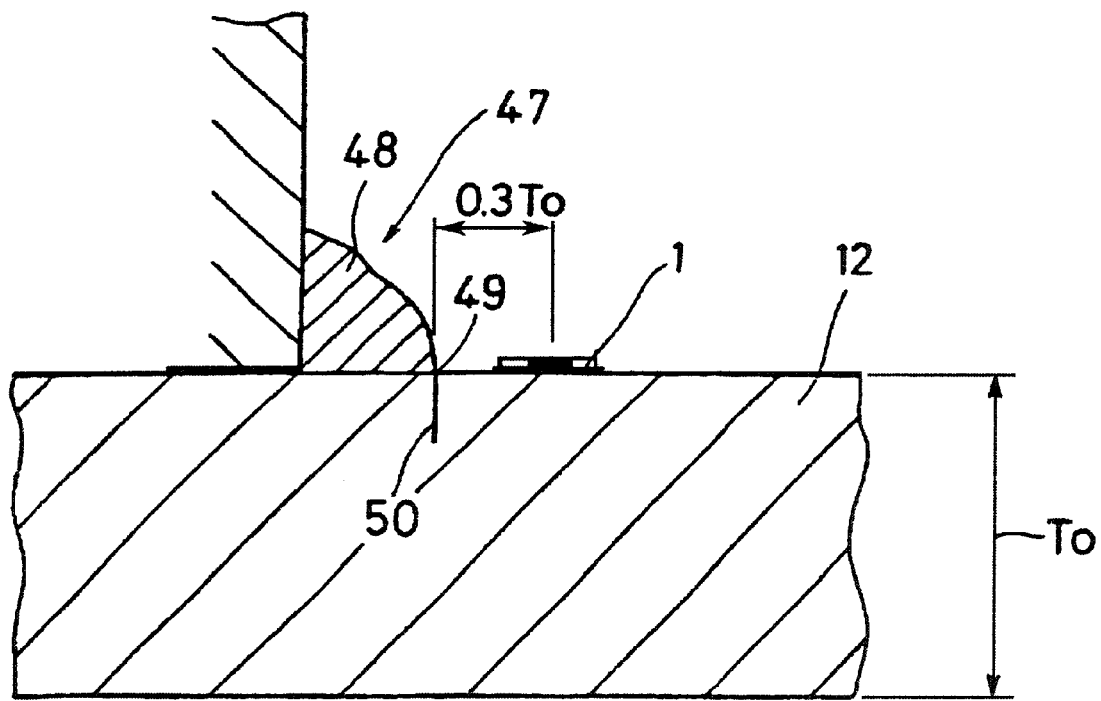
FIG. 6 is a view showing a state in which the crack-type fatigue detecting sensor of FIG. 1 is attached to a vicinity of a welded bead of a member to be tested.

The fatigue detecting sensor 1 is used to measure fatigue damage of a welded structure, for example. FIG. 6 shows a state in which the fatigue detecting sensor 1 is attached to a vicinity of the welded bead 48 of the member 12. In general, when the life of the welded structure expires, a fatigue crack 50 has occurred and has propagated from the weld toe 49 of the welded bead 48 of a fillet welded joint 47 of the member 12. A parameter called hot spot stress on a local portion of the structure is capable totally evaluating the fatigue life of the welded structure. Using an S–N diagram of a simple cruciform filet welded joint, the fatigue life can be evaluated. The hot spot stress as defined herein refers to stress at the weld toe 49 of the welded bead 48, which includes stress concentrated due to structural discontinuity but does not include stress concentrated due to a shape of the welded bead 48. The hot spot stress is represented by a position (0.3×thickness To of the member) apart from the weld bead toe 49 to be evaluated.

Thus, the position representative of the hot spot stress is clearly defined. The fatigue detecting sensor 1 is attached to or in the vicinity of the weld toe 49 and used for measurement. By way of example, if the thickness To of a member to be tested of a ship structure is 20–30 mm, the position at which measurement is to be made is 6–10 mm apart from the weld bead toe 49. When the length of the fatigue detecting sensor 1 in the longitudinal direction is 70 mm or more like the conventional sensor, measurement at the position at which the hot spot stress is generated is impossible, and it is therefore necessary to estimate data at the position at which the hot spot stress is generated, by one method pr another. However, the estimated data entails an error. On the other hand, in this embodiment, the length L1 of the fatigue detecting sensor 1 is 13 mm and it is therefore possible to attach the sensor at a position 6.5 mm or more apart from the weld bead toe 49 and make measurement at the position at which the hot spot stress is generated. In this case, the thickness of the member 12 is 22 mm and measurement can be directly made at the position at which the hot spot stress is generated. The measured data does not entail an error.

Figure 7:
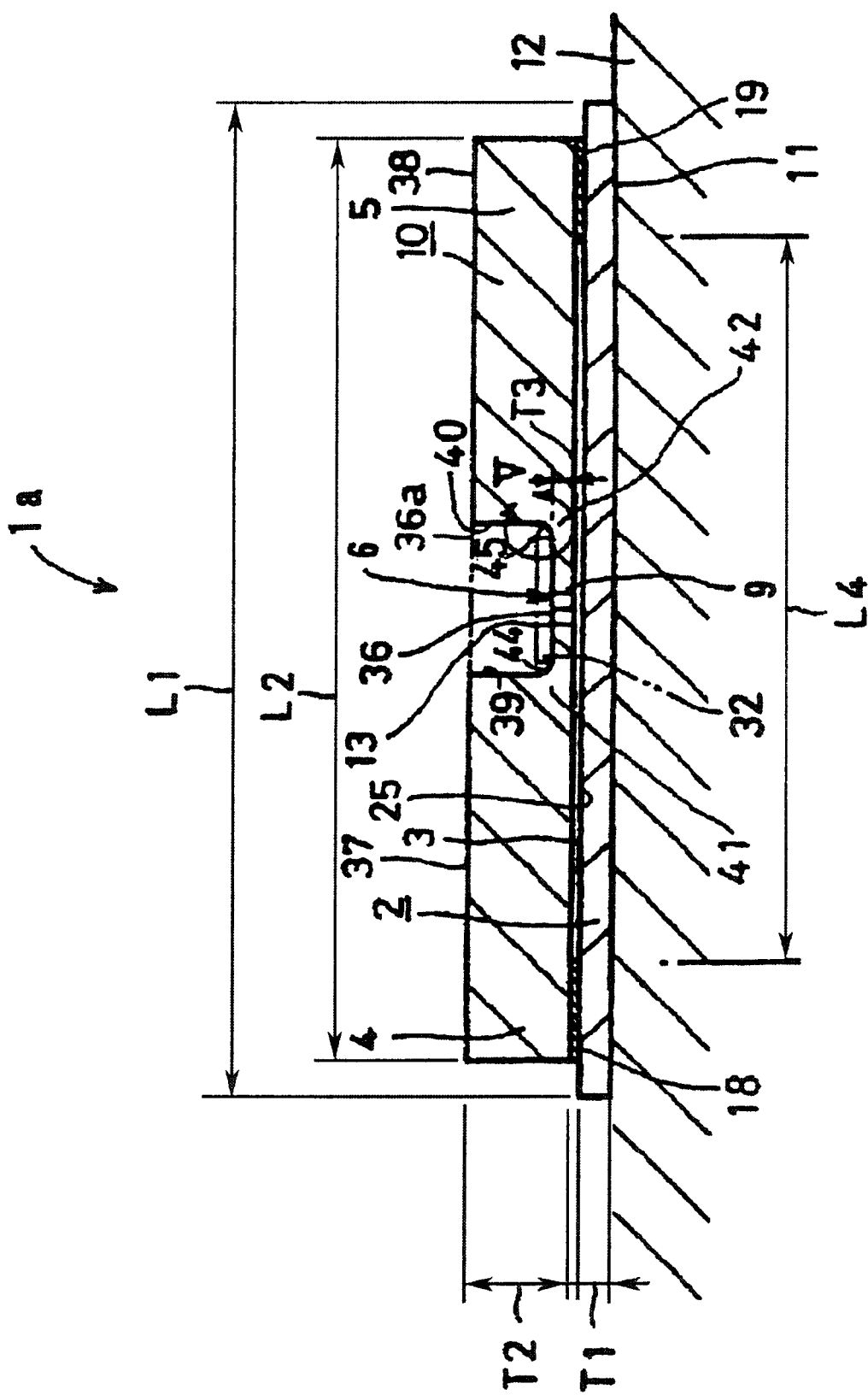
FIG. 7 is a cross-sectional view showing a crack-type fatigue detecting sensor according to another embodiment of the present invention.
Figure 8:
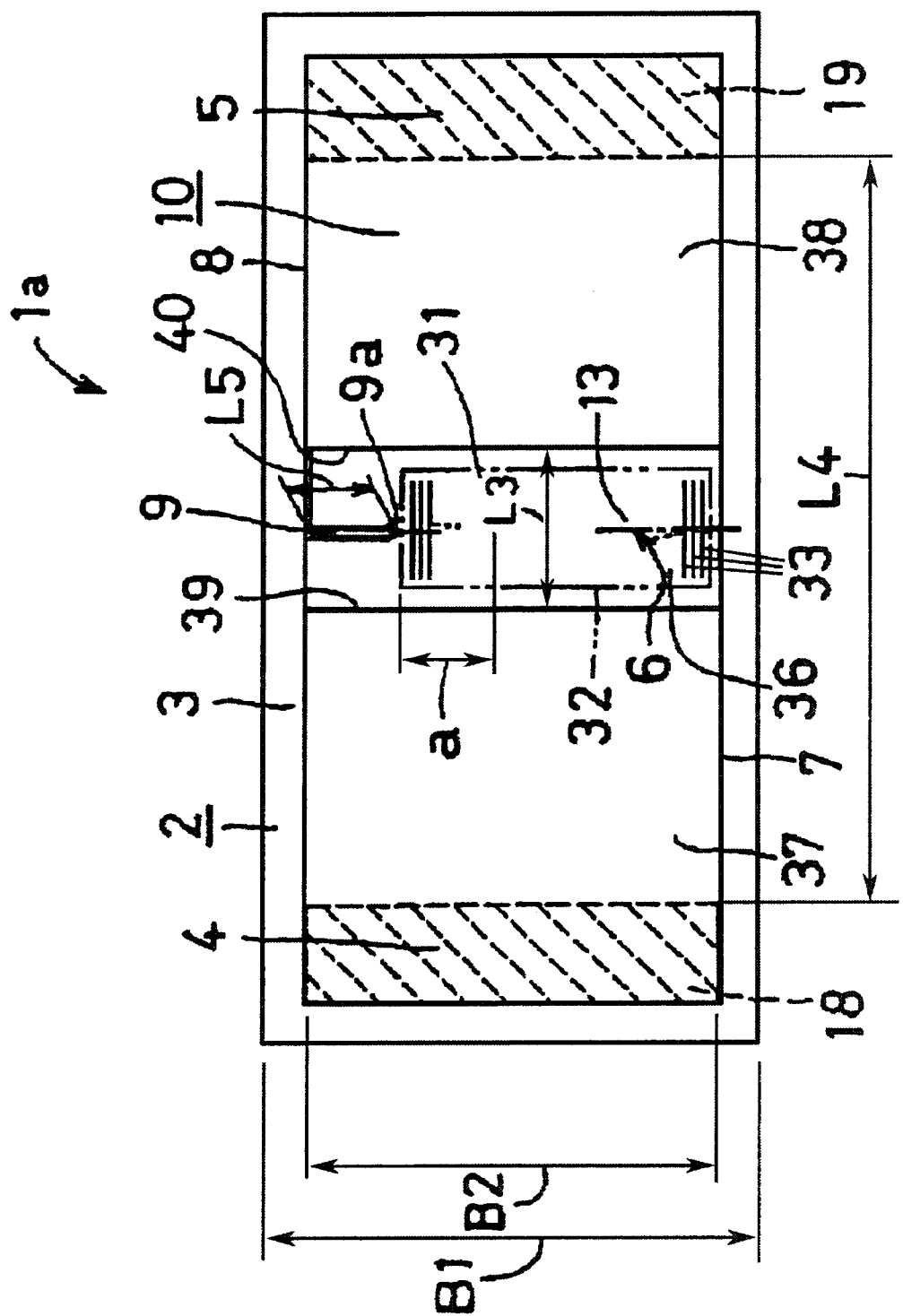
FIG. 8 is a plan view showing the crack-type fatigue detecting sensor of FIG. 7.

FIG. 7 is a cross-sectional view showing a crack-type fatigue detecting sensor 1a according to another embodiment of the present invention and FIG. 8 is a plan view showing a crack-type fatigue detecting sensor 1a of FIG. 7. In these Figures, the reference numerals of this embodiment denotes the same or corresponding parts of the above-described embodiment and will not be discussed to avoid repetition. The crack-type fatigue detecting sensor 1a of this embodiment corresponds to examples 3, 4 listed in Tables 1 through 3 mentioned later, in which the fracture piece 10 made of pure Ni is joined to the surface 3 of the substrate 2 made of Invar via bonding layers 18, 19. With this configuration, the same effects as the crack-type fatigue detecting sensor 1 of the embodiment mentioned previously is achieved and the sensor can be easily fabricated because the substrate 2 and the fracture piece 10 can be joined without troubles. As can be seen from the Table 2, the bonding layers 18, 19 may be realized by bonding sheets (corresponding to samples 9–11), or by phenol based bond (corresponding to samples 12, 13). When the phenol based bond is used, an unbonded region of the fracture piece 10 is covered with a polyimide film for preventing this region from being bonded, and the bond is applied thereto.

Subsequently, as shown in Table 1, to confirm sensitivity of the fatigue detecting sensor 1, the inventors created samples 1–15 by changing dimensions, shapes and materials of the substrate 2 and the fracture piece 10 in comparisons 1, 2 and examples 1–5.

TABLE 1

| | | | fracture piece | | | substrate | |
|---|---|---|---|---|---|---|---|
| type | | material | thickness ratio [mm/mm] intermediate portion 13/end portions 4,5 | span L4 × width B2 × slit length L5 [mm] | | material | length L1 × width B1 × thickness T1 [mm] |
| comparison 1 | sample 1 | pure Ni | 0.02/0.02 | 3 × 2.5 × 0.5 | | polyimide | 7 × 3.5 × 0.025 |
| | sample 2 | pure Ni | 0.02/0.02 (width change) | 5 × 2.5 × 0.5, (5) | | polyimide | 10 × 8.5 × 0.025 |
| comparison 2 | sample 3 | pure Ni | 0.01/0.04 | 5 × 5 × 1 | | polyimide | 10 × 6 × 0.025 |
| | sample 4 | pure Ni | 0.02/0.04 (width 2 step) | 5 × 2.5 × 0.5, (5) | | polyimide | 10 × 6 × 0.025 |
| example 1 | sample 5 | pure Ni | 0.02/0.10 | 8 × 5 × 1 | | polyimide | 13 × 6 × 0.025 |
| | sample 6 | pure Ni | 0.02/0.10 | 15 × 7.5 × 1.5 | | polyimide | 22 × 8.5 × 0.025 |
| example 2 | sample 7 | pure Ni | 0.02/0.10 | 8 × 5 × 1 | | polyimide | 13 × 6 × 0.025 |
| | sample 8 | pure Ni | 0.02/0.10 | 15 × 7.5 × 1.5 | | polyimide | 22 × 8.5 × 0.025 |
| example 3 | sample 9 | pure Ni | 0.01/0.04 | 5 × 5 × 1 | | Invar | 10 × 6 × 0.05 |
| | sample 10 | pure Ni | 0.02/0.10 | 8 × 5 × 1 | | Invar | 13 × 6 × 0.05 |
| | sample 11 | pure Ni | 0.02/0.10 | 15 × 7.5 × 1.6 | | Invar | 22 × 8.5 × 0.05 |
| example 4 | sample 12 | pure Ni | 0.02/0.10 | 8 × 5 × 1 | | Invar | 13 × 6 × 0.05 |
| | sample 13 | pure Ni | 0.02/0.10 | 15 × 7.5 × 1.5 | | Invar | 22 × 8.5 × 0.05 |
| example 5 | sample 14 | pure Ni | 0.02/0.10 | 9.6 × 5 × 1 | | Invar | 13 × 6 × 0.05 |
| | sample 15 | pure Ni | 0.02/0.10 | 18.4 × 7.5 × 1.5 | | Invar | 22 × 8.5 × 0.05 |

In Table 1, the sample 1 of the comparison 1 disclosed in Japanese laid-Open Patent Publication No. Hei. 10-185854 (Japanese Patent No. 25-2576) and the sample 2 of the comparison 1 disclosed in Japanese Patent No. 25-2594 are listed. In the comparison 2, as a method for improving strain sensitivity, (a) a method for making the thickness T3 of the intermediate portion 13 of the fracture piece 10 small, and (b) a method for making the width B2 of the fracture piece 10 small, were employed and these methods (a), (b) were employed in the samples 3, 4.

The examples 1, 2 (samples 5–8) were designed so that the sensors have twice to three times strain sensitivity as high as strain sensitivity of the conventional fatigue detecting sensor of the comparison 1. Among the samples 5–8, the samples 5, 7 were created by joining the fracture piece 10 to the substrate 2 such that the surface 36 of the intermediate portion 13 and the upper surface 3 of the substrate 2 face each other and the samples 6, 8 were created by joining them as shown in FIG. 1. Also, among the samples 5–8, the samples 5, 7 were configured such that a separation film covering the surface of the bond was attached to the bond for bonding the fracture piece 10 and the substrate 2 to prevent attachment of the bond to the end portions 4, 5. As can be seen from Table 2, between the examples 1, 2, press conditions in which the fracture piece 10 and the substrate 2 were joined differed from each other and temperature management conditions after press, differed from each other.

TABLE 2

| | | Joint method of fracture piece and substrate | | | |
|---|---|---|---|---|---|
| type | | joint means | bonding thickness [mm] | press condition: temperature × pressure × pressurizing time | after cure: temperature × time |
| comparison 1 | sample 1 | epoxy based bond | 0.02 | 150° C. × 15 kgf/cm² × 15 min | 130° C. × 2 hr |
| | sample 2 | epoxy based bond | 0.02 | 150° C. × 15 kgf/cm² × 15 min | 130° C. × 2 hr |
| comparison 2 | sample 3 | epoxy based bond | 0.02 | 150° C. × 15 kgf/cm² × 15 min | 130° C. × 2 hr |
| | sample 4 | epoxy based bond | 0.02 | 150° C. × 15 kgf/cm² × 15 min | 130° C. × 2 hr |
| example 1 | sample 5 | epoxy based bond | 0.02 | 150° C. × 15 kgf/cm² × 15 min | 130° C. × 2 hr |
| | sample 6 | epoxy based bond | 0.02 | 150° C. × 15 kgf/cm² × 15 min | 130° C. × 2 hr |
| example 2 | sample 7 | epoxy based bond | 0.02 | room temperature 0.5 kgf/cm² × 24 hr | — |
| | sample 8 | epoxy based bond | 0.02 | room temperature 0.5 kgf/cm² × 24 hr | — |
| example 3 | sample 9 | bonding sheet | 0.04 | 160° C. × 30 kgf/cm² × 30 min | — |
| | sample 10 | bonding sheet | 0.04 | 160° C. × 30 kgf/cm² × 30 min | — |
| | sample 11 | bonding sheet | 0.04 | 160° C. × 30 kgf/cm² × 30 min | — |
| example 4 | sample 12 | phenol based bond + polyimide film | 0.02~ 0.04 | 80° C. × 5 kgf/cm² × 1 hr + 150° C. × 5 kgf/cm² × 3 hr | — |
| | sample 13 | phenol based bond + polyimide film | 0.02~ 0.04 | 80° C. × 5 kgf/cm² × 1 hr + 150° C. × 5 kgf/cm² × 3 hr | — |
| example 5 | sample 14 | PGRM | 0 | 70° C. | — |
| | sample 15 | PGRM | 0 | 70° C. | — |

In the example 3, the material of the substrate 2 was changed from polyamide (examples 1, 2) to Invar, the means for bonding the fracture piece 10 and the substrate 2 was changed from the epoxy based bond (examples 1, 2) to bonding sheets, and temperature at which the fracture piece 10 and the substrate 2 were joined was determined to cause the tensile residual stress to be generated on the fracture piece 10. In the example 4, the means for bonding the fracture piece 10 and the substrate 2 was changed from the bonding sheets (example 3) to the phenol based bond and the polyimide film and the joint welding condition was changed. The examples 3, 4 correspond to the embodiment of FIGS. 7, 8.

In the example 5, the electric resistance welding was employed as the joint method. The temperature at which the fracture piece 10 and the substrate 2 were joined was set to 70° C. The sample 14 of the example 5 corresponds to the fatigue detecting sensor 1 of FIGS. 1 through 6.

Under these conditions, characteristics of the samples 1–15 were evaluated and the results were shown in Table 3.

the crack propagated at measurement point P5 as shown in FIG. 10(5) (number of repeated load cycles $N=2.1\times10^5$, length a of crack propagation =2.90 mm), the crack propagated at measurement P6 as shown in FIG. 10(6) (number of repeated load cycles $N=2.7\times10^5$, length a of crack propagation =3.75 mm), and the crack propagated at measurement P7 as shown in FIG. 10(7) (number of repeated load cycles $N=3.0\times10^5$, length a of crack propagation =3.95 mm).

In the sample 15 about twice as long as the sample 14, the crack propagated at measurement point Q1 as shown in FIG. 11(1) (number of repeated load cycles N=0, length a of crack propagation =0.45 mm), the crack propagated at measure-

TABLE 3

| type | | analysis value | "strain" sensitivity and "stress" sensitivity (steel number) | | repeated load | | |
|---|---|---|---|---|---|---|---|
| | | K value per unit stress: K/D | strain range $\Delta_\epsilon$ [$\times 10^{-6}$] | stress range $\Delta_\sigma$ [kgf/mm$^2$] | cylces to failure of fracture piece: N | stress ratio: R | remark column |
| comparison 1 | sample 1 | 1.10 | 1,100 | 23.1 | $1.10 \times 10^6$ | 0 | |
| | sample 2 | 1.38 | 800 | 16.8 | $1.10 \times 10^6$ | 0 | |
| comparison 2 | sample 3 | 1.85 | 900 | 18.8 | $8.50 \times 10^5$ | 0 | unstable, inferior quality |
| | sample 4 | 1.65 | 800 | 16.8 | $3.20 \times 10^5$ | 0 | |
| example 1 | sample 5 | 2.87 | 449 | 9.4 | $5.10 \times 10^5$ | 0 | |
| | sample 6 | 4.39 | 253 | 5.3 | $2.12 \times 10^6$ | 0 | |
| example 2 | sample 7 | 2.87 | 373 | 7.8 | $1.92 \times 10^6$ | 0 | |
| | sample 8 | 4.39 | 249 | 5.2 | $3.10 \times 10^6$ | 0 | |
| example 3 | sample 9 | 1.85 | >500 | 10.5 | $>2.27 \times 10^6$ | 0 | crack (−) |
| | sample 10 | 2.87 | >500 | 10.5 | $>2.27 \times 10^6$ | 0 | crack (−) |
| | sample 11 | 4.39 | >500 | 10.5 | $>2.27 \times 10^6$ | 0 | crack (−) |
| example 4 | sample 12 | 2.87 | 237 | 5.0 | $2.30 \times 10^6$ | 0 | |
| | | | 241 | 5.1 | $3.96 \times 10^6$ | −1 | |
| | sample 13 | 4.39 | 184 | 3.8 | $(6.75 \times 10^5)$ | 0 | |
| | | | 269 | 5.6 | $(3.80 \times 10^5)$ | −1 | |
| example 5 | sample 14 | 3.40 | 283 | 5.9 | $(6.00 \times 10^5)$ | 0 | |
| | | | 275 | 5.8 | $(1.30 \times 10^6)$ | −1 | |
| | sample 15 | 5.26 | 182 | 3.8 | $(7.00 \times 10^5)$ | 0 | |
| | | | 179 | 3.8 | $(1.10 \times 10^6)$ | −1 | |

As can be seen from Table 3, strain range $\Delta\epsilon$ and stress range $\Delta\sigma$ were employed as characteristics for evaluation of sensitivity of the fatigue detecting sensor. With regard to the strain range $\Delta\epsilon$, it was confirmed that the sample 5 of the example 1 had approximately twice strain sensitivity as high as strain sensitivity of the sample 1 of the comparison 1. With regard to the stress range $\Delta\sigma$, it was confirmed that the sample 5 of the example 1 was improved about 2.5 times compared with the sample 1.

Figure 9:
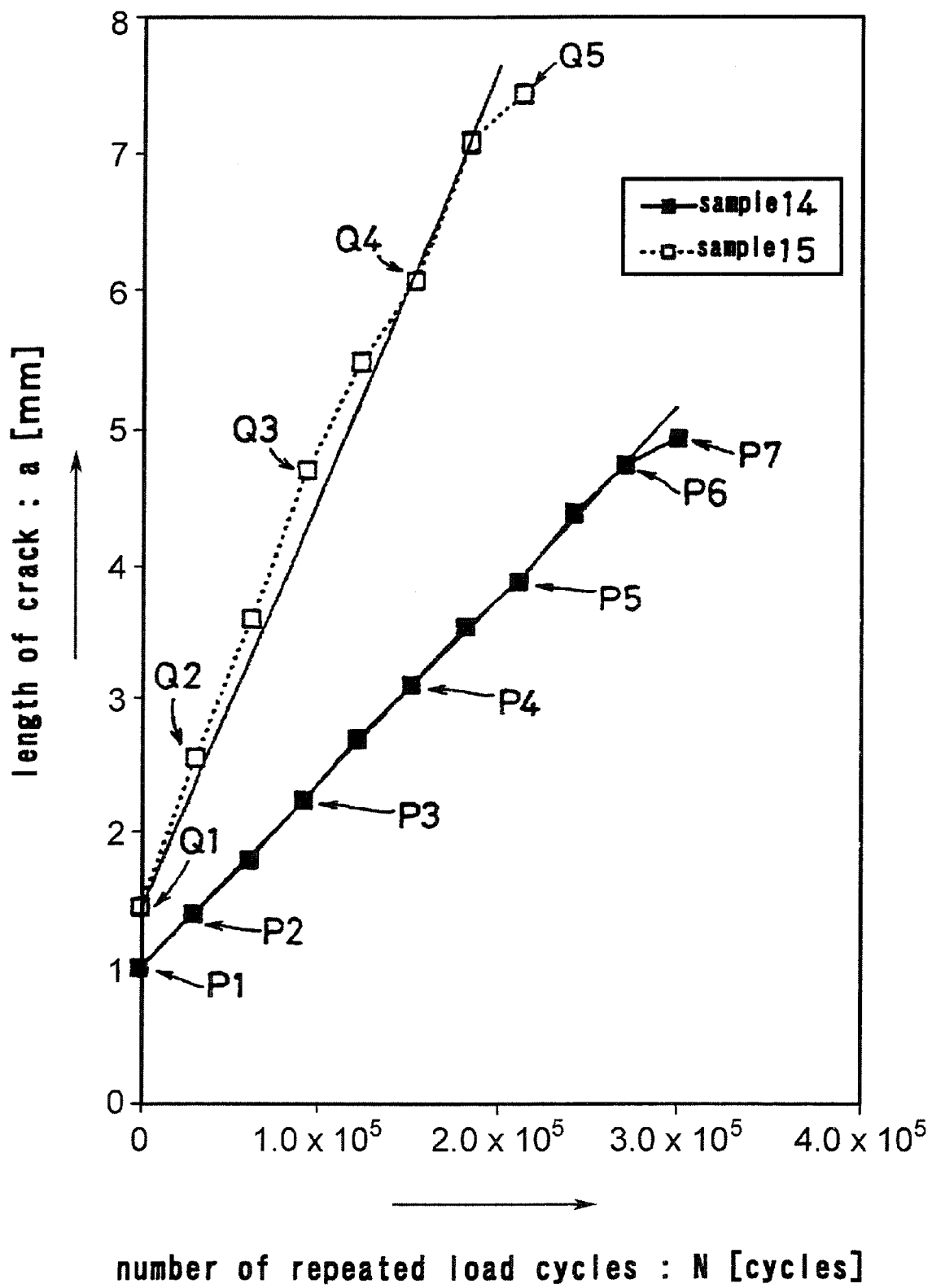
FIG. 9 is a graph showing relationship between number of repeated load cycles N and length a of crack propagation of samples 14, 15 when $\Delta\epsilon=500\times10^{-6}$ as an example of strain range of a member to be tested.

FIG. 9 is a graph showing relationship between number of repeated load cycles N and length a of crack propagation of the samples 14, 15 when the strain range of the member to be tested is $\Delta\epsilon=500\times10^{-6}$. FIG. 10 is a plan view showing crack propagation states of the sample 14 in FIG. 19 at measurement points P1–P7. FIG. 11 is a plan view showing crack propagation states of the sample 15 in FIG. 9 at measurement points Q1–Q5. In the sample 14 corresponding to the fatigue detecting sensor 1 of the embodiment shown in FIGS. 1–6, the crack did not propagate at measurement point P1 as shown in FIG. 10(1) (number of repeated load cycles N=0, length a of crack propagation =0.00 mm), the crack propagated at measurement point P2 as shown in FIG. 10(2) (number of repeated load cycles $N=0.3\times10^5$, length a of crack propagation =0.40 mm), the crack propagated at measurement point 3 as shown in FIG. 10(3) (number of repeated load cycles $N=0.9\times10^5$, length a of crack propagation =1.25 mm), the crack propagated at measurement point P4 as shown in FIG. 10(4) (number of repeated load cycles $N=1.5\times10^5$, length a of crack propagation =2.10 mm), ment point Q2 as shown in FIG. 11(2) (number of repeated load cycles $N=0.3\times10^5$, length a of crack propagation =1.55 mm), the crack propagated at measurement point Q3 as shown in FIG. 11(3) (number of repeated load cycles $N=0.9\times10^5$, length a of crack propagation =3.70 mm), the crack propagated at measurement point Q4 as shown in FIG. 11(4) (number of repeated load cycles $N=1.5\times10^5$, length a of crack propagation =5.10 mm), the crack propagated at measurement point Q5 as shown in FIG. 11(5) (number of repeated load cycles $N=2.1 \times10^5$, length a of crack propagation =6.45 mm).

Figure 12:
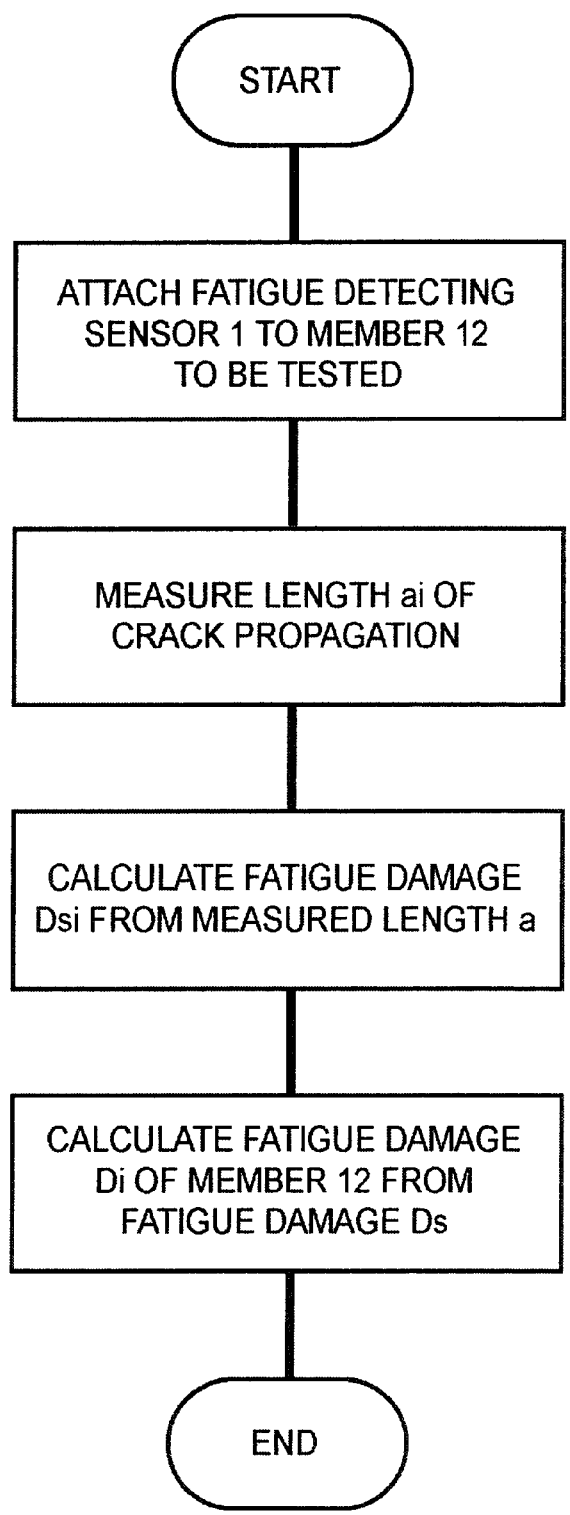
FIG. 12 is a flow chart for explaining a procedure for estimating fatigue damage according to one gauge method using the crack-type fatigue detecting sensor of FIG. 1.

FIG. 12 is a flow chart for explaining a procedure for estimating fatigue damage according to one gauge method using the fatigue detecting sensor 1. In general, as a method for predicting fatigue damage of the member to be tested, a two gauge method using two fatigue detecting sensors and the one gauge method using one fatigue detecting sensor are known. In the two gauge method, it is necessary to select materials in which gradients of characteristic curves showing relationship between crack propagation speed da/dn and a stress intensity factor $\Delta K$, greatly differ from each other. For the sake of simplicity, the fatigue detecting sensor with the gradient equal to the gradient of the S-N diagram of the member to be tested for which damage is evaluated and with fatigue strength smaller than fatigue strength of the member to be tested, can be used to measure fatigue damage according to the one gauge method. The procedure will be explained below.

Initially, in step s1, the fatigue detecting sensor 1 was attached to the member 12 as shown in FIG. 6, and in step s2, length a of crack propagation was measured by using the fatigue detecting sensor 1. The length a of crack propagation may be electrically measured by the measuring means 32. Alternatively, the crack propagation region 31 may be imaged by using a fiber scope and processed by an image processing device, and the resulting image data may be used to obtain the length a of crack propagation.

Figure 13:
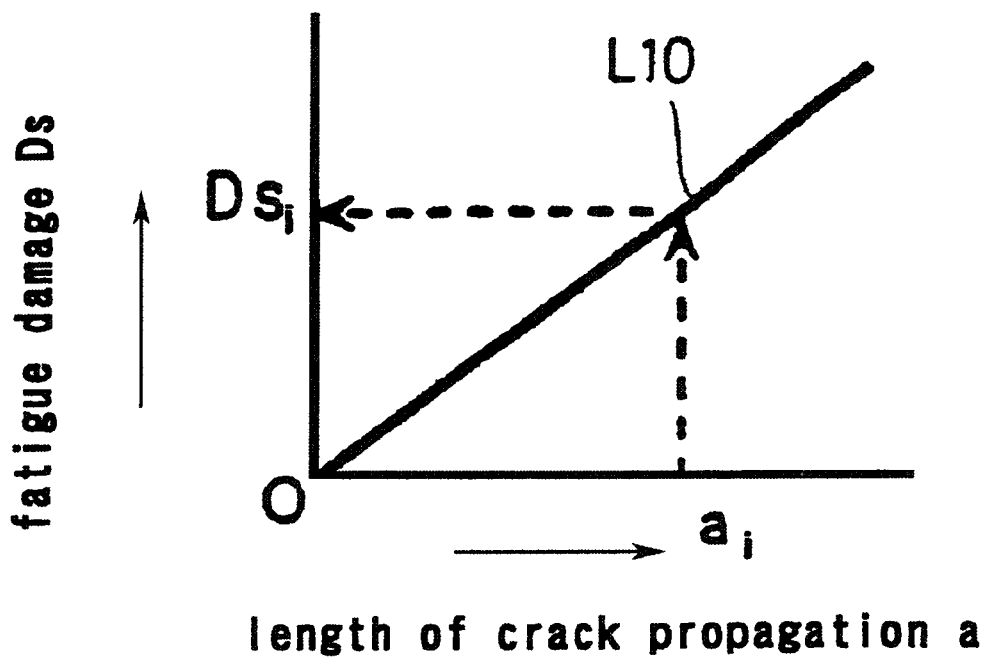
FIG. 13 is a view showing relationship between the length a of crack propagation measured by the crack-type fatigue detecting sensor of FIG. 1 and corresponding fatigue damage Ds.
Figure 14:
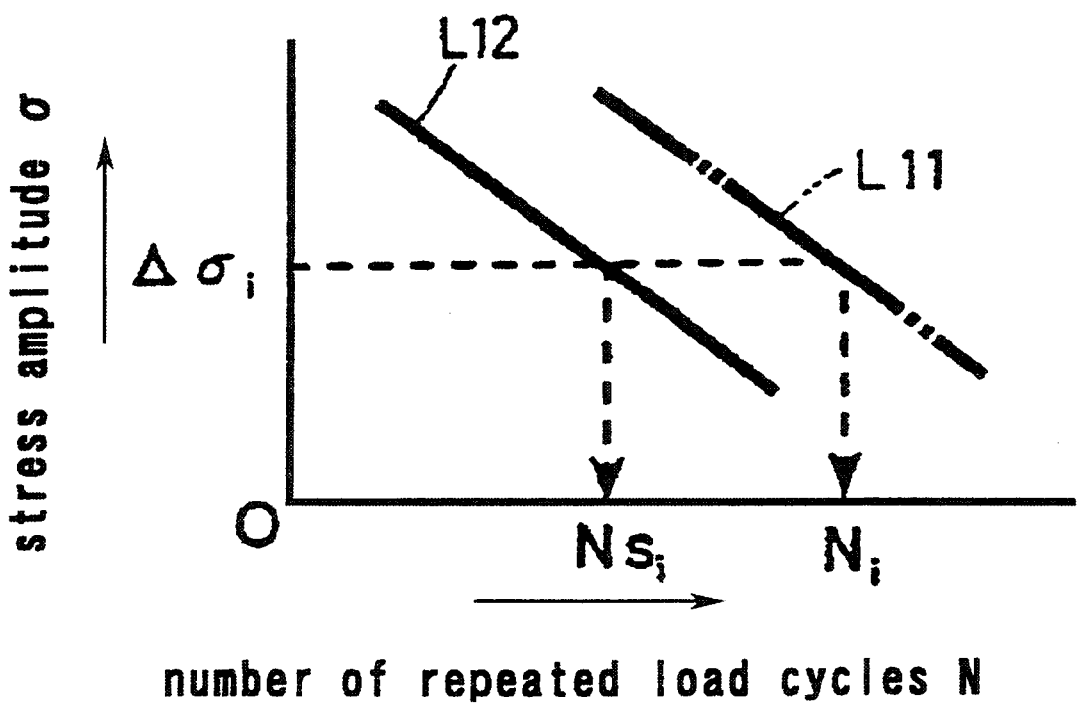
FIG. 14 is a view showing an S-N characteristic of the crack-type fatigue detecting sensor of FIG. 1, which is associated with an S-N characteristic of the member to be tested.
Figure 15:
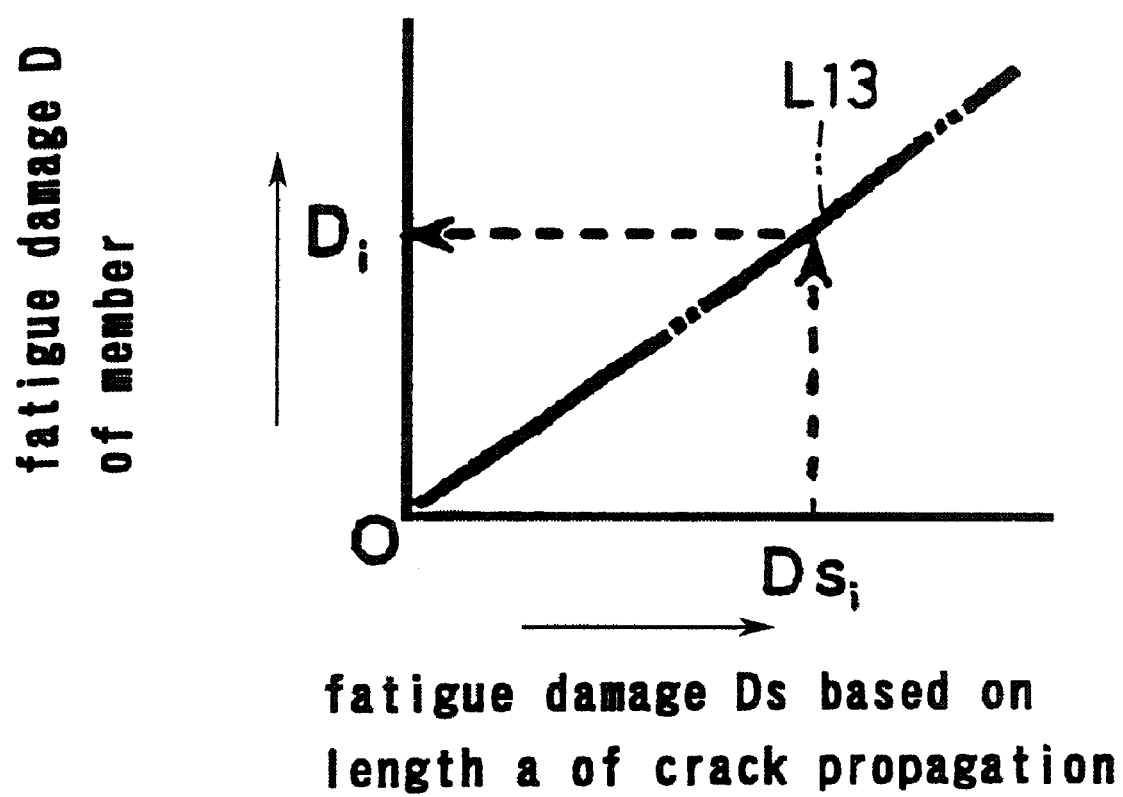
FIG. 15 is a view for estimating fatigue damage of the member to be tested, which is associated with the fatigue damage Ds calculated based on the length a of crack propagation of the crack-type fatigue detecting sensor of FIG. 1.

In step S3, fatigue damage Ds associated with length ai of crack propagation of the crack occurring in the fatigue detecting sensor, was found. Based on a line L10 showing relationship between the length a of crack propagation and the fatigue damage Ds in FIG. 13, fatigue damage Dsi of the fatigue detecting sensor 1 was calculated. As shown in FIG. 14, a line L12 showing a characteristic of the fatigue detecting sensor 1 that is parallel with a line L11 showing the characteristic of the member 12 and having a slope in the S-N diagram equal to the slope of the fatigue detecting sensor 1 was found in advance. In step s4, based on a line L 13 showing relationship between damage of the fatigue detecting sensor 1 and damage of the member 12 in FIG. 15, the fatigue damage Di of the member 12 associated with the fatigue damage Dsi calculated based on the length ai of the crack propagation of the fatigue detecting sensor 1 is calculated and estimated. It should be noted that a longitudinal axis indicating a stress amplitude σ and a lateral axis indicating the number of repeated load cycles N are a common logarithmic scale.

In still another embodiment, the fatigue detecting sensor 1 according to the invention may be adapted to estimate the fatigue damage by the two gauge method.

Numerous modifications and alternative embodiments of the invention will be apparent to those skilled in the art in view of the foregoing description. Accordingly, the description is to be construed as illustrative only, and is provided for the purpose of teaching those skilled in the art the best mode of carrying out the invention. The details of the structure and/or function may be varied substantially without departing from the spirit of the invention and all modifications which come within the scope of the appended claims are reserved.

What is claimed is:

1. A crack-type fatigue detecting sensor comprising:
   a foil substrate having a first surface and having a second surface for being fixed to a solid target to be tested; and
   a foil fracture piece having opposite end portions, a central portion between the opposite end portions relative to a longitudinal direction of the fracture piece, and a slit within the central portion and extending from one side portion toward the other side portion in a width direction transverse to the longitudinal direction of the fracture piece, wherein
   the opposite end portions of the fracture piece are respectively fixed to the first surface of the foil substrate, and wherein a portion including the central portion and the slit has a thickness smaller than a thickness of the opposite end portions over a whole width of the fracture piece.

2. The crack-type fatigue detecting sensor according to claim 1, wherein the fracture piece with tensile stress remaining thereon is fixed to the first surface of the foil substrate at the opposite end portions.

3. The crack-type fatigue detecting sensor according to claim 1, wherein the fracture piece is directly joined to the first surface of the foil substrate at the opposite end portions or indirectly joined to the first surface at the opposite end portions utilizing a bonding layer.

4. The crack-type fatigue detecting sensor according to claim 1, wherein the fracture piece is provided with a means for electrically measuring a length of crack propagation in a region from a tip end portion of the slit to the other side portion in the width direction, on which the crack develops.

5. The crack-type fatigue detecting sensor according to claim 1, wherein the slit formed in the fracture piece has a tip end portion that is pointed in a direction from the one side portion toward the other side portion in the width direction.

6. The crack-type fatigue detecting sensor according to claim 1, wherein
   the fracture piece has a first surface associated with the central portion, a second surface associated with each of the opposite end portions, and a step face formed between the first surface and each of the second surfaces such that the step faces are vertically provided with the slit situated between the step faces, and a convex curved portion at which each of the step faces transitions into the first surface.

7. The crack-type fatigue detecting sensor according to claim 1, wherein a ratio L3/L4 of a length L3 of the central portion in the longitudinal direction to a length L4 of an unjoined region between the opposite end portions is used to adjust sensitivity in such a manner that the sensitivity is made higher as the ratio L3/L4 is decreased.

8. A method for fabricating a crack-type fatigue detecting sensor comprising the steps of:
   forming a foil film having opposite end portions, an intermediate portion between the opposite end portions relative to a longitudinal direction of the foil film, by electroforming plating, and a slit in a central portion of the intermediate portion extending from one side portion toward the other side portion in a width direction transverse to the longitudinal direction of the foil film;
   after covering the foil film, except the intermediate portion including the central portion having the slit with a resist film, forming a fracture region in the exposed intermediate portion having a predetermined reduced thickness by etching; and
   joining the opposite end portions of the foil film to a substrate.

9. A method for fabricating a crack-type fatigue detecting sensor comprising the steps of:
   forming a foil film having opposite end portions, an intermediate portion between the opposite end portions relative to a longitudinal direction of the foil film, a slit in a central portion of the intermediate portion extending from one side portion toward the other side portion in a width direction transverse to the longitudinal direction of the foil film;
   after covering the foil film, except the intermediate portion including the central portion having the slit with a resist film, forming a fracture region in the exposed intermediate portion having a predetermined reduced thickness by etching; and
   joining the opposite end portions of the foil film to the substrate made of a material having a linear expansion coefficient lower than a linear expansion coefficient of a material of the fracture region at a predetermined elevated temperature higher than a normal temperature.

10. The method for fabricating the crack-type fatigue detecting sensor according to claim 8, wherein the foil film is directly joined to the substrate at the opposite end portions or indirectly joined to the substrate at the opposite end portions utilizing a bonding layer by electric resistance welding.

11. The method for fabricating the crack-type fatigue detecting sensor according to claim 9, wherein the foil film is directly joined to the substrate at the opposite end portions or indirectly joined to the substrate at the opposite end portions utilizing a bonding layer by electric resistance welding.

12. The method for fabricating the crack-type fatigue detecting sensor according to claim 9, wherein a ratio L3/L4 of a length L3 of the intermediate portion of the foil film in the longitudinal direction to a length L4 of an unjoined region between the opposite end portions in the longitudinal direction is used to adjust sensitivity in such a manner that the sensitivity is made higher as the ratio L3/L4 is decreased.

13. A method for estimating damage using a crack-type fatigue detecting sensor comprising the steps of:

providing a foil substrate having a first surface and a second surface;

fabricating a foil fracture piece having opposite end portions, a central portion between the opposite end portions relative to a longitudinal direction of the fracture piece, and a slit within the central portion and extending from one side portion toward the other side portion in a width direction transverse to the longitudinal direction of the fracture piece, wherein the slit has a thickness smaller than a thickness of the opposite end portions over a whole width of the fracture piece;

respectively fixing the opposite end portions of the fracture piece to the first surface of the substrate;

fixing the second surface of the substrate to a test specimen;

measuring a length of crack propagation during a predetermined period; and estimating damage of the member to be tested based on the length of crack propagation.

* * * * *